United States Patent [19]

Jacobs et al.

[11] Patent Number: 4,943,414
[45] Date of Patent: Jul. 24, 1990

[54] METHOD FOR VAPOR STERILIZATON OF ARTICLES HAVING LUMENS

[75] Inventors: Paul T. Jacobs; Ronald F. Berry, both of Arlington; Toby A. Soto, Fort Worth, all of Tex.

[73] Assignee: Johnson & Johnson Medical, Inc., Arlington, Tex.

[21] Appl. No.: 79,550

[22] Filed: Jul. 30, 1987

[51] Int. Cl.⁵ .............................................. A61L 2/20
[52] U.S. Cl. ................................ 422/28; 220/85 F; 220/87; 220/DIG. 7; 422/294; 422/305
[58] Field of Search .................. 422/28, 294, 305; 220/85 F, 87, DIG. 7

[56] References Cited

U.S. PATENT DOCUMENTS

| | | | |
|---|---|---|---|
| 1,403,461 | 1/1922 | Van Meter | 422/294 X |
| 1,817,530 | 4/1931 | Spanel | 422/294 |
| 3,371,985 | 3/1968 | Wyka | 422/305 X |
| 4,380,530 | 4/1983 | Kaye | 422/300 |
| 4,410,492 | 10/1983 | Kaye | 422/27 |
| 4,424,189 | 1/1984 | Hick | 422/28 X |
| 4,744,951 | 5/1988 | Cummings et al. | 422/28 |

Primary Examiner—Robert J. Warden
Assistant Examiner—Jill Johnston
Attorney, Agent, or Firm—Joseph F. Shirtz

[57] ABSTRACT

A method and device for enhancing the vapor sterilization of the lumen of medical instruments and like articles under reduced pressure. A vessel containing a small amount of a vaporizable liquid sterilant solution is attached to the lumen. The sterilant vaporizes and flows directly into the lumen of the article as the pressure is reduced for the sterilization cycle.

10 Claims, 3 Drawing Sheets

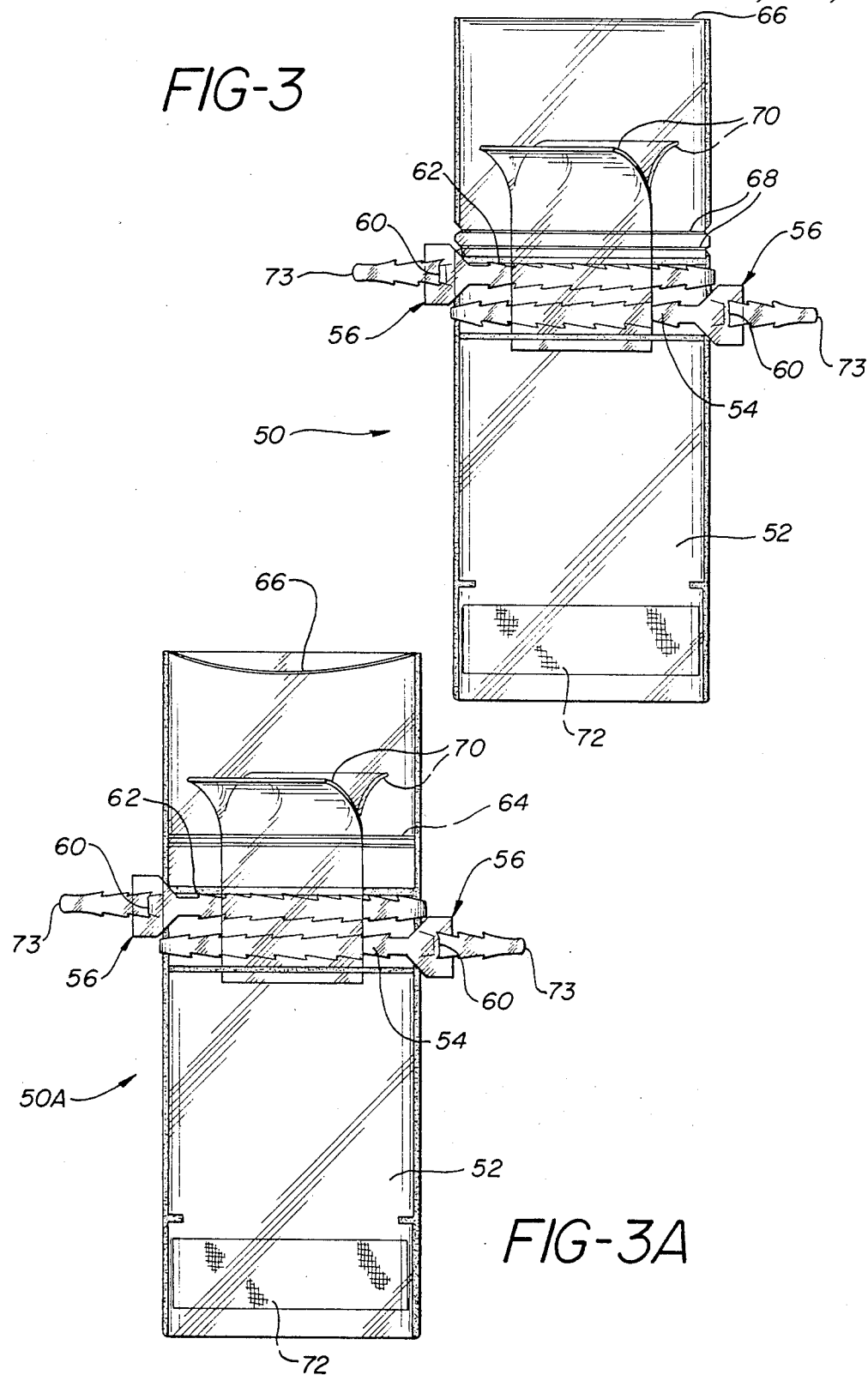

METHOD FOR VAPOR STERILIZATON OF ARTICLES HAVING LUMENS

FIELD OF THE INVENTION

The invention relates to the vapor sterilization of articles such as medical instruments having long narrow lumens therein, and more particularly, to a device for delivering a gaseous sterilant directly into the lumen of an article during the sterilization process.

BACKGROUND OF THE INVENTION

The need to sterilize articles such as medical instruments and others for use in the agriculture and fermentation industries is well known. In recent years, many methods of vapor sterilization have been developed. While these methods offer the advantage of being generally faster than sterilization by immersion in a sterilant solution, they suffer from one major disadvantage, namely the inability to sterilize the interior of a long narrow tube in a short period of time. Thus, with regard to medical instruments such as endoscopes, the difficulty in sterilizing the lumen can often negate the general advantage of using vapor sterilization.

One way of overcoming the above disadvantage is set forth in U.S. Pat. Nos. 4,410,492 and 4,337,223. The apparatus described therein comprises a sterilizing chamber with means for introducing a sterilant gas into the chamber and circulating the gas within the chamber. Disposed within the chamber is a socket for receiving the tubular end of a medical instrument. The socket is connected to a valve and a recirculating pump and the sterilant gas is recirculated from the chamber through the lumen of the instrument. The commercial apparatus, using ethylene oxide and water as the sterilant, has had little commercial success which may be attributable to the extended sterilization times of about 3 hours for flexible endoscopes and about 2 hours for the shorter, rigid endoscopes, as well as to the toxicity problems associated with ethylene oxide sterilization. In addition, the method and apparatus described in these references cannot be used to sterilize an instrument within a sterile pack since one end of the instrument must be attached to the socket.

Thus there is a current need for an effective method to sterilize medical instruments such as endoscopes in a reasonably short period of time, preferably in one hour or less. The method and device of the present invention makes vapor sterilization of such instruments practical by delivering vapor directly to the interior of the lumen in the endoscope, whether or not it is in a sterile pack.

SUMMARY OF THE INVENTION

The present invention comprises a method and device for providing antimicrobial vapor directly into the long narrow lumen of medical instruments and similar articles. The device and method are intended for use with solution vapor sterilization procedures. In these procedures, the article is placed within a sterilization chamber, the pressure in the chamber is reduced, and a liquid solution of an antimicrobial agent is introduced into the chamber where it vaporizes. Alternatively, an antimicrobial vapor may be introduced directly to the chamber after the pressure therein has been reduced. In either case, the instrument is sterilized by exposure to the vapor or an active species generated from it rather than by direct contact with a liquid sterilant. The procedure may further involve the use of heat or, e.g., low pressure gas plasma to enhance the antimicrobial activity, reduce sterilization times, and/or remove residual sterilant from the instrument.

In its simplest form, the device of the present invention comprises a vessel containing a small amount of the antimicrobial solution, and a means for connecting the vessel to the lumen of the instrument to provide a source of antimicrobial vapor directly to the lumen during the vapor sterilization process. The device is placed on the instrument prior to disposing the instrument in the sterilization chamber. As the pressure in the chamber is reduced, the antimicrobial solution contained in the vessel is vaporized and passes from the vessel into the lumen of the instrument. In its simplest form, the means of connecting the vessel to the end of the instrument tube may comprise something as simple as a piece of firm but flexible tubing, such as tygon tubing of appropriate diameter such that one end of the tubing may be inserted in or disposed about the opening of the vessel, and the end inserted in or disposed about the lumen of the instrument so as to be securely join the two. However, the preferred means described below provide more adjustable fastening and may be used with instruments having a wide variation in internal and external tube diameters. With the use of the device and method of the present invention, vapor sterilization times for endoscopes can be reduced to one hour or less. In addition, the method and the device may be used to sterilize endoscopes in a sterile pack since the device of the present invention may be attached to and packaged with the endoscope before the endoscope is placed within the sterilization chamber. Upon opening of the pack, the device may be retrieved for re-use or discarded with the pack.

In one preferred embodiment of the device of the present invention, the means for connecting the vessel to the end of the tube comprises an expandable sheath, one end of which is securely attached about an opening in the vessel, and the other end of which comprises an elastic ring for making a releasable attachment about the end of a tubular instrument. Where the vessel of the device includes a rim or lip about the opening, the sheath may be attached to the vessel by means of a second elastic ring disposed over such lip or rim.

In another embodiment of the device of the present invention, the means for connecting the vessel to the end of the instrument comprises a flexible bushing disposed within the opening of the vessel. The bushing may be made of a series of rings of inwardly extending plastic flaps. The vessel may be provided with means for attaching a closure cap thereto, such as threads internal or external to the opening of the vessel for attaching a screw cap or plug, to maintain the antimicrobial solution in the vessel prior to use. Alternatively, the vessel may be provided with an aperture for attaching a disposable cartridge containing a premeasured aliquot of antimicrobial solution.

In another embodiment, the vessel comprises a flexible pouch, and the means for connecting the vessel to the end of the instrument tube comprises a drawstring disposed about the opening of the pouch. The pouch may be provided with an airtight seal for sealing the antimicrobial solution therein prior to use, and a means for creating an opening in the sealed pouch so that the pouch may be disposed about the end of the instrument when desired.

Both the seal and the means for creating an opening may be achieved with, for instance, a "zip-lock" interlocking channel and ridge type fastening across the opening of the pouch. As an alternative, the pouch may be heat sealed and provided with scoring, notches, or other known means for tearing open the pouch.

The device and method of the present invention reduce sterilization time required for instruments having long narrow lumens therein. Reduced sterilization times are also achieved with the instruments encased in a package designed to maintain sterility after the removal from the sterilized chamber. In addition, as antimicrobial vapor is provided directly into the lumen of the instrument, lower concentrations of antimicrobial solutions may be used in the sterilizer, and this together with the reduced sterilization times provides improved materials compatibility with respect to both the instrument components and the packaging or wrapping materials.

BRIEF DESCRIPTION OF THE DRAWINGS

FIG. 3 is a plan view of another embodiment of a device of the present invention.

FIG. 3A is a variation of the device of FIG. 3.

DETAILED DESCRIPTION OF THE INVENTION

Figure 1:
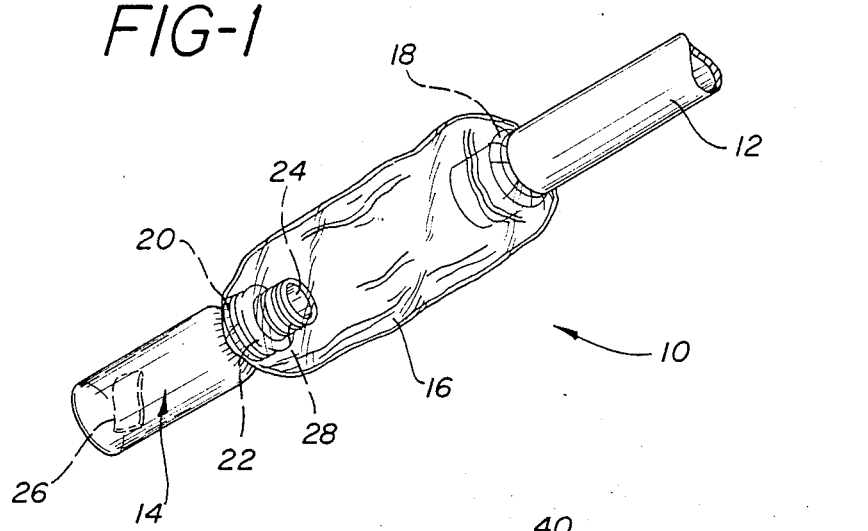
FIG. 1 is a perspective view of one embodiment of the device of the present invention, attached to the end of a tube.

The method and device of the present invention relates to the sterilization of articles such as medical instruments having a long narrow tube therein. The term instruments as used herein applies to medical or surgical devices such as endoscopes, catheters, tubing, or similar instruments or articles having an internal lumen which is preferably used in a sterile condition as in, for example, the agricultural or fermentation industries. The method and device of the present application show particular advantages in the solution vapor sterilization of lumens exceeding ten centimeters in length and having an internal diameter of about 7 millimeters or less. As endoscopes typically have lumens with internal diameters of 1 to 4 millimeters and lengths of up to 1.5 meters or more for flexible endoscopes and at least 45 centimeters for rigid endoscopes, the method and device of the present application have particular applicability to the sterilization of these instruments. With the use of the device of the present invention, antimicrobial vapor is supplied directly to the lumen or interior of the tube of the instrument during the vapor sterilization process.

The antimicrobials used with the method and device of the present invention include solutions of glutaraldehyde, hydrogen peroxide, chlorine dioxide or other antimicrobials in an inert solvent, the only requirement being that the solution be liquid at atmospheric pressure and a vapor at the temperature and pressure of the sterilization process. Though the higher concentration solutions of antimicrobials are more effective, problems with materials compatibility and shipping and handling may arise at very high concentrations. For example, a 30% to 50% solution of hydrogen peroxide in water is both very effective and presents few shipping and handling problems, while higher concentrations of up to 70% become increasingly more difficult and dangerous to handle.

In solution vapor sterilization, the procedure generally used is as follows: The article to be sterilized is placed within the sterilization chamber, the chamber is sealed, and a vacuum is drawn on the chamber to reduce the pressure to less than about 50 torr, and preferably to 20 torr or less. An antimicrobial solution is then injected into the chamber where it vaporizes and contacts the exposed surfaces of article. The time necessary for total kill of specific microbial agents varies with the type and concentration of antimicrobials present, and with the degree of exposure to the microbial agent. Microbials disposed in cracks, crevices or internal tubular structures are somewhat protected from the antimicrobial agent and require more time for total kill than microbials on the external surface of the article. Heat or high frequency radiation may be used to increase the effectiveness of the antimicrobial and its penetration into remote areas of the instrument.

The device of the present invention comprises a vessel for containing a small amount of antimicrobial solution, and a means for connecting the vessel directly to the lumen or the end of the tube of the article to be sterilized. When the article with device containing antimicrobial solution is disposed in the sterilization chamber and a vacuum drawn on the chamber, antimicrobial vapor generated from the solution within the vessel flows directly into the lumen.

The effectiveness of the method and device of the present invention was demonstrated by the following experiments:

50 inch (127 centimeters) lengths of tygon tubing having a 2 millimeter inside diameter were used to simulate an endoscope in the sterilization test. A paper strip (2 mm × 13 mm) containing approximately $2.0 \times 10^6$ *Bacillus subtilis* (var. globigii) spores was placed in each tube equidistant from each end. A syringe containing 0.05 milliliters of 10% by weight hydrogen peroxide solution in water was provided for each tube. Each of the samples was individually packaged in a TYVEK TM /MYLAR TM envelope prior to sterilization.

One third of the samples (three units) were placed in the package with the syringe unattached to the end of the tube. Another one-third of the samples were packaged with the syringe attached. Individual samples were placed within a 65 liter sterilization chamber and sent through a hydrogen peroxide vapor sterilization cycle wherein the pressure within the chamber was reduced to 3 torr for the total exposure time minus 15 minutes, and 0.5 torr for the final 15 minutes of exposure. No additional hydrogen peroxide was injected into the chamber.

The remaining one-third of the samples, packaged with the syringe attached to the end of the tube as described above, were sent through a hydrogen peroxide vapor sterilization cycle supplemented with high frequency radiation plasma which is known to generate an active species from the hydrogen peroxide. Again a 65 liter chamber was used, and the pressure within the chamber was reduced to 3.0 torr for the total exposure time minus 15 minutes and 0.5 torr for the final 15 minutes of exposure. Again, no additional hydrogen peroxide was injected into the chamber. Plasma was generated only during the final 15 minutes of exposure at 2.05 MHz with 320 watts of power, pulsed 0.3 milliseconds on to 1.0 milliseconds off.

At the conclusion of the sterilization cycle, the paper strip was removed from each tube and placed in a glass vial containing 10 mls of a sterile pH 7.0 phosphate buffer solution. This solution contained 10 milligrams of TWEEN 80 to aid in removal of any spores from the paper strip and 0.0066 milligram of catalase to neutralize any remaining hydrogen peroxide. Five glass beads were placed in the solution, and the solution was vortexed for two minutes to completely mascerate the paper strip. Three decimal dilutions of the solution were made with sterile pH 7.0 phosphate buffer, and the original solution and the decimal dilutions were poured into sterile glass Petri plates. A culture medium was added and the plates were incubated for four days at 30° C. After incubation the number of viable organisms in each plate was counted, and the number of spores on the paper strip calculated by multiplying the spore count by the appropriate dilution factor.

Figure 4:
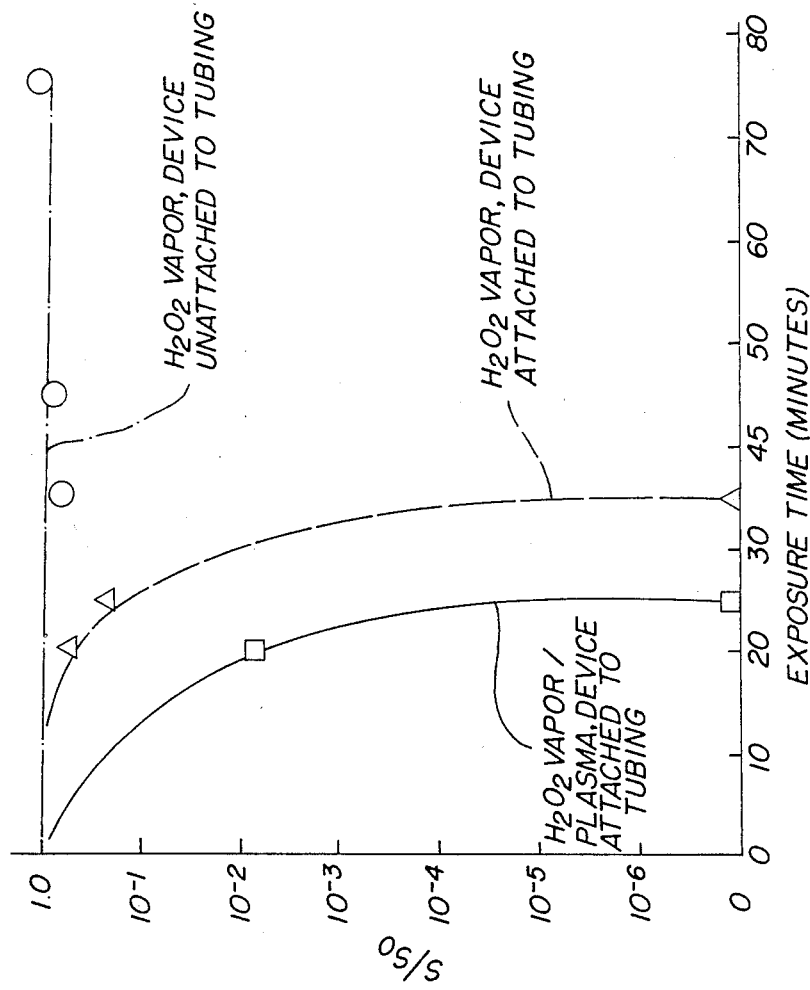

The results of the experiments are presented in Table I below, and plotted in FIG. 4, where $S/S_0$ represents the ratio of the number of organisms surviving the test to the initial number of organisms which were placed on the paper strip prior to the test. As shown by these data, no reduction in microbial population was achieved in samples where the syringe was unattached to the tubing, even after an exposure time of 75 minutes. Attaching the syringe to the end of the tube according to the method of the present invention produced total kill in 35 minutes without low temperature gas plasma, and in 25 minutes when the antimicrobial activity was enhanced by the use of low temperature gas plasma.

TABLE I

| Sample | Sterilization Time - Min. | Efficacy (S/So) |
| --- | --- | --- |
| A | 35 | $8.6 \times 10^{-1}$ |
|   | 45 | $8.9 \times 10^{-1}$ |
|   | 75 | $1.1 \times 10^{0}$ |
| B | 20 | $7.0 \times 10^{-1}$ |
|   | 25 | $5.8 \times 10^{-1}$ |
|   | 35 | 0 |
| C | 20 | $8.5 \times 10^{-3}$ |
|   | 25 | 0 |
|   | 35 | 0 |

Sample A - Syringe unattached
Sample B - Syringe attached
Sample C - Syringe attached plus plasma A preferred embodiment of the device to be used in accordance with the teaching of the present invention is shown in FIG. 1. The device indicated generally at 10 is shown attached to a tube 12. In the device depicted in FIG. 1, the means for connecting the vessel 14 to the end of the tube comprises an expandable sheath 16, one end of which is securely attached to the vessel, and the other end of which comprises an elastic ring 18 making a releasable attachment about the end of the tube. The sheath 16 may be attached to the vessel in any known manner and, as shown in FIG. 1, the sheath 16 is attached to the vessel by a second elastic ring 20 disposed over the lip 22 about opening 24 of vessel 14. Though the vessel shown is cylindrical, the vessel may comprise any three dimensional container preferably of semi-rigid material, having an opening therein. The vessel may be made of, e.g., polyethylene, polypropylene, glass or any other material which is nonreactive to the antimicrobial solution of vapor. The sheath may also be formed of polyethylene, polypropylene or other material which is relatively nonreactive to the antimicrobial vapor. The elastic rings may be formed of natural latex or butyl rubber which are relatively resistant to the sterilant vapors; however, resistivity is less critical when the device is constructed for one time use. Disposed within the vessel may be a substrate 26 comprising a woven or nonwoven fabric or sponge for containing the liquid antimicrobial solution. The vessel preferably has a means 28 associated with the opening for attaching a closure cap over the opening prior to use in order to maintain the antimicrobial solution therein. As shown in FIG. 1, means 28 comprises threads for a screw cap fitting about the lip of the vessel.

Figure 2:
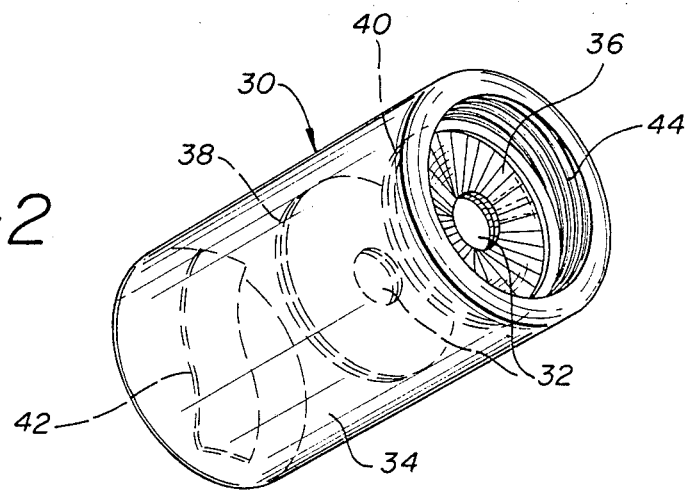
FIG. 2 is a perspective view of another embodiment of the device of the present invention, showing the end of the device for making a connection to a tubular member.

Another embodiment of the device of the present invention is depicted in FIG. 2 where the device is indicated generally at 30. The means for connecting the vessel 34 to the end of a tubular instrument comprises a bushing 36 disposed within the open end of the vessel. In the particular embodiment shown in FIG. 2, the bushing comprises a series of rings 38 and 40 of inwardly extending plastic flaps defining a flexible aperture 32 to receive the tubular instrument. The flaps can be made of any flexible material which is non reactive to the antimicrobial solution or vapor, such as polyethylene, and of sufficient thickness that the flaps provide resistance to withdrawal of a tube inserted through the aperture.

Disposed within the vessel is a substrate 42 containing the antimicrobial solution. Preferably, the vessel 34 is provided with means 44 for attaching a closure cap thereto prior to use. As shown in FIG. 2, means 44 comprise threads for attaching a screw cap (not shown) within the opening of the vessel.

Figure 2A:
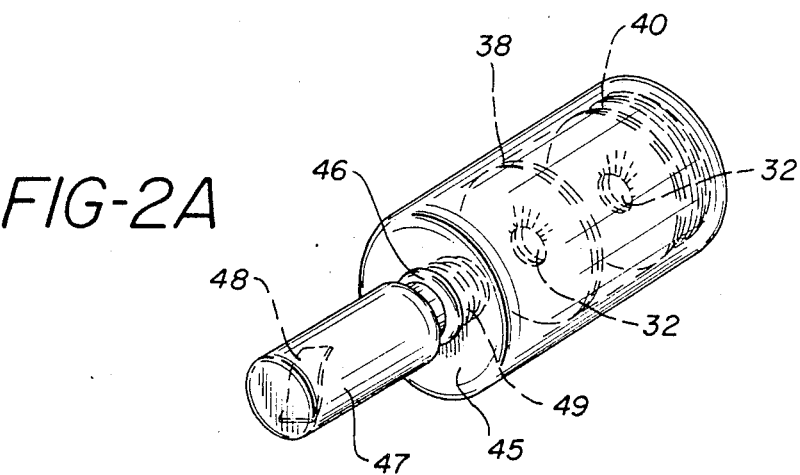
FIG. 2A is a variation of the device of FIG. 2.

FIG. 2A illustrates a variation in the design of the device of FIG. 2 which utilizes the same basic vessel and means for attachment to a tubular device. In the device shown in FIG. 2A, end 45 of the vessel opposite the open end is provided with aperture 46 for attaching a disposable cartridge 47 containing a supply of antimicrobial on a substrate such as a woven or nonwoven fabric or sponge 48 as illustrated. The aperture 46 of the vessel is designed in conjunction with neck 49 of the cartridge to provide quick and easy attachment and release of the cartridge and the vessel. In the embodiment shown in FIG. 2A, aperture 46 is provided with reverse threads for engaging the threads of the neck 49 of the cartridge. In this variation of the device it is not necessary for a substrate contain the antimicrobial solution to be disposed within the vessel since the antimicrobial solution is provided in premeasured aliquots in the cartridges. With the device of FIG. 2A one achieves the convenience and accuracy of disposable, premeasured aliquots of antimicrobial solution without the expense associated with the device of FIG. 2.

The following table sets forth the effectiveness of the devices depicted in FIGS. 1 and 2 in a sterilization procedure described below.

TABLE II

Effect of Devices on Efficay of Sterilization Inside Tubes

| Material | I.D. (cm) | Length (cm) | Efficacy (S/So) |  |  |
| --- | --- | --- | --- | --- | --- |
|  |  |  | No. Device | Device FIG. 1 | FIG. 2A |
| Surgical Tygon | 0.64 | 10 | 0 | — | — |
|  | 0.64 | 20 | $4.4 \times 10^{-5}$ | — | — |
|  | 0.64 | 30 | $1.1 \times 10^{-2}$ | — | — |
|  | 0.64 | 45 | $8.8 \times 10^{-1}$ | 0 | 0 |
| Rubber tubing | 0.64 | 25 | $1.7 \times 10^{-1}$ | — | — |
|  | 0.64 | 45 | $7.9 \times 10^{-1}$ | 0 | 0 |

The efficacy as recorded in terms of the ratio of the number of microorganisms surviving the test, S, to the number of challenge organisms, $S_0$ (approx. $1 \times 10^6$), on a paper strip disposed within the tube equidistant from the ends. In the sterilization procedure, 100 microliters of 30% aqueous $H_2O_2$ solution was supplied in each of the devices. The devices were attached to the ends of tubes of the indicated length and 0.64 cm in internal diameter. All of the tube samples were placed within TYVEK TM /MYLAR TM packaging prior to sterilization. The packaged tubes were placed within the sterilizing chamber and the pressure therein was reduced to about 0.1 torr in about 10 minutes. Additional 30% $H_2O_2$ solution was injected into the chamber to achieve a concentration of 2.0 milligrams $H_2P_2$ per liter of chamber volume. Following injection of the $H_2O_2$, the tubes were retained in the chamber an additional 50 minutes.

Injection of the $H_2O_2$ solution raised the pressure in the chamber to about 6 torr and the pressure was again reduced to about 0.1 torr. During the last 10 minutes of exposure, low temperature gas plasma was generated in the chamber at 300 watts. The challenge micro organisms used in the test were *Bacillus subtilis* (var. globigii) spores.

As shown in Table II above, when the tube length was only 10 centimeters, sterilization was achieved without the use of the device according to the present invention. However, for tubing of 20 and 30 centimeters in length, a device of the present invention would be needed in order to achieve sterility within the exposure time of the test. For tubes of 45 centimeters in length, total kill was achieved during the 1 hour exposure time of the test, using either of the devices depicted in FIG. 1 and FIG. 2.

A further experiment utilizing 1 mm medical grade Teflon tubing 183 cm in length. The tubing was cut into three pieces to obtain a 5 cm long center section which was joined to the end sections by external tubing connectors. In the experiment, approximately $1.0 \times 10^4$ *Bacillus subtilis* (var. globigii) spores were deposited in the center section of the Teflon tubing, and the tubing assembled and subjected to sterilization with hydrogen peroxide vapor as described above at a concentration of 2.0 mg/liter of chamber volume. The chamber was evacuated to a pressure of 0.1 torr before the peroxide was injected as a 30% aqueous solution and allowed to vaporize. After 20 minutes, a continuous gas plasma was generated in the chamber at 300 watts 13.5 $MgH_2$ and the sterilization continued for an additional 5 minutes after which the vacuum was released with sterile, filtered air, and the number of surviving spores determined.

The experiment was first conducted without a device of the present invention attached to the tubing, then repeated with a device of FIG. 3 as described below containing 100 ml of 30% hydrogen peroxide attached to one end of the tubing. The experimental results of the tests are presented in Table III below.

TABLE III

Sterilization of 1 mm Tubing

| Material | I.D. | Length | Efficacy (S/So) | |
|---|---|---|---|---|
| | | | No Device | Fig. 1 Device |
| Teflon | 1 mm | 183 cm | $1.9 \times 10^{-1}$ | 0 |

The data of Table III demonstrate the efficacy of the method of the present invention in sterilizing the lumen of very long tubes having very small diameters as often used in certain endoscopic procedures.

Additional embodiments of the device of the present invention are depicted in FIGS. 3 and 3A. The device shown in FIG. 3 indicated generally at 50, comprises a vessel 52 in the form of a pouch constructed of a flexible material. The means for connecting the vessel or pouch 52 to the end of an instrument tube comprises a first drawstring 54, and preferably a second drawstring 62. These drawstrings are preferably arranged in the configuration as shown in FIG. 2 to be drawn from opposite sides of the pouch. The pouch is preferably provided with an airtight seal to maintain the antimicrobial solution therein prior to use, and includes a means for creating an opening in the sealed pouch so that it may be disposed over the end of a tube. The seal may be created by sealing the ends 66 of the pouch, and the means for opening the sealed pouch may comprise, for example, a line of weakening at 68, preferably in combination with a notch also shown generally at 68, to permit the pouch to be opened by tearing off one end.

FIG. 3A shows a device indicated generally at 50A, similar to device 50, but wherein the airtight seal and the means for creating and opening the sealed pouch is a line of fastening 64 similar to a "zip-lock" closure. Optionally, opening flaps 70 may be provided on either side of the pouch adjacent closure 64 of FIG. 3A, or the line of weakening 68 of FIG. 3. These flaps are firmly secured to the pouch. In use, after the sealed end 66 of the pouch of FIG. 3 has been removed along the line of weakening 68, the flaps when pulled oppositely from each other will distend the opening of the pouch for disposal around the end of an instrument tube. The flaps of FIG. 3A, when pulled in opposite directions, can be used to open the zip-lock fastening, or if the fastening is already opened, to distend the opening for disposal around the end of an instrument tube. A substrate 72 such as a woven or nonwoven fabric or sponge may be disposed within the pouch for containing the antimicrobial solution.

In a preferred construction, the drawstrings are provided with a locking means as illustrated. Though many means for locking or catching a drawstring are known in the art and may be used in conjunction with the present invention, the locking means depicted at 56 at FIG. 3 comprise a catch 60 for a serrated edge 58 provided on the drawstring. As shown in FIG. 3, the catch, comprising an opening for disposing one end of the drawstring therethrough, is located at the opposite end of the drawstring. The catch, however, may be provided by a flap, with opening therein, attached to the edge of the pouch, provided the other end of the drawstring must also be attached to the pouch. When two drawstrings are used, one or both drawstrings may be provided with a locking means. By pulling the end 73 of the drawstring, the flexible pouch is gathered and a firm fastening may be made to a tube inserted within the pouch.

Although the present invention has been described in terms of specific devices for use in a preferred method of vapor sterilization, it will be understood that various modifications in the device and method will be apparent to those skilled in the art and are within the scope of this invention.

We claim:

1. In a method for vapor sterilization of an article having a narrow lumen therein which comprises disposing the article within a chamber, evacuating the chamber, and introducing a first supply of antimicrobial vapor into said chamber to contact and sterilize said article, the improvement comprising connecting a vessel containing a second supply of antimicrobial solution to the lumen of said article prior to disposing the article in the chamber whereby antimicrobial vapor derived from said second supply of antimicrobial solution is introduced directly into said lumen of said article.

2. The method of claim 1 wherein said antimicrobial is hydrogen peroxide.

3. The method of claim 2 wherein said antimicrobial solution is a 20 to 50 percent by weight aqueous solution of hydrogen peroxide.

4. The method of claim 1 wherein said vessel is connected to the lumen of said article by means of an expandable flexible sheath.

5. The method of claim 1 wherein said article and said vessel containing the second supply of antimicrobial solution attached thereto is packaged in an air permeable, bacterial barrier material prior to being disposed in the chamber.

6. The method of claim 5 wherein said article is a medical instrument.

7. The method of claim 6 wherein said medical instrument is an endoscope.

8. The method of claim 5 wherein said article is tubing.

9. The method of claim 1 wherein said chamber is evacuated to a pressure of less than about 50 torr.

10. The method of claim 1 wherein said chamber is maintained at a pressure of less than 20 torr while said antimicrobial vapor is in contact with said article.

* * * * *